United States Patent [19]

Ronel et al.

[11] 4,298,002

[45] Nov. 3, 1981

[54] POROUS HYDROPHILIC MATERIALS, CHAMBERS THEREFROM, AND DEVICES COMPRISING SUCH CHAMBERS AND BIOLOGICALLY ACTIVE TISSUE AND METHODS OF PREPARATION

[75] Inventors: Samuel H. Ronel, Princeton; Mark J. D'Andrea, Neshanic Station, both of N.J.; William H. Dobelle; Gregory F. Klomp, both of New York, N.Y.; Hiroshi Hashiguchi, Riverdale, N.Y.

[73] Assignee: National Patent Development Corporation, New York, N.Y.

[21] Appl. No.: 73,680

[22] Filed: Sep. 10, 1979

[51] Int. Cl.³ .............................................. A61M 7/00
[52] U.S. Cl. ...................................... 128/260; 424/19; 424/81; 521/61
[58] Field of Search ................ 128/130, 260, 261, 268; 424/14–22, 81; 521/61

[56] References Cited

U.S. PATENT DOCUMENTS

| | | | |
|---|---|---|---|
| 3,093,831 | 6/1963 | Jordan | 128/260 |
| 3,279,996 | 10/1966 | Long, Jr. et al. | 128/260 |
| 3,428,043 | 2/1969 | Shepherd | 128/268 |
| 3,499,862 | 3/1970 | Wichterle . | |
| 3,551,556 | 12/1970 | Kliment et al. | 424/21 |
| 3,574,826 | 4/1971 | Shepherd et al. | 424/81 |
| 3,576,760 | 4/1971 | Gould et al. . | |
| 3,577,512 | 5/1971 | Shepherd et al. | 424/21 |
| 3,641,237 | 2/1972 | Gould et al. | 424/16 |
| 3,660,071 | 5/1972 | Gould et al. . | |
| 3,660,563 | 5/1972 | Gould et al. | 424/81 |
| 3,670,073 | 6/1972 | Shepherd et al. | 424/47 |
| 3,681,089 | 8/1972 | Gould et al. . | |
| 3,681,248 | 8/1972 | Gould et al. . | |
| 3,689,634 | 9/1972 | Kliment et al. | 424/21 |
| 3,699,089 | 10/1972 | Wichterle et al. . | |
| 3,737,521 | 6/1973 | Born | 424/22 |
| 3,765,414 | 10/1973 | Arlen | 128/260 |
| 3,767,790 | 10/1973 | Guttag | 424/81 |
| 3,772,215 | 11/1973 | Gould et al. . | |
| 3,818,894 | 6/1974 | Wichterle et al. | 128/334 R |
| 3,821,087 | 6/1974 | Knazek et al. . | |
| 3,825,458 | 7/1974 | Wichterle et al. . | |
| 3,857,932 | 12/1974 | Shepherd et al. | 424/19 |
| 3,860,490 | 1/1975 | Guttag . | |
| 3,862,452 | 1/1975 | Wichterle et al. . | |
| 3,873,423 | 3/1975 | Munder et al. . | |
| 3,881,026 | 4/1975 | Shepherd et al. . | |
| 3,885,078 | 5/1975 | Wichterle et al. . | |
| 3,888,975 | 6/1975 | Ramwell | 128/260 |
| 3,896,806 | 7/1975 | Wichterle | 128/260 |
| 3,896,819 | 7/1975 | Zaffaroni et al. | 128/260 |
| 3,948,732 | 4/1976 | Haddad et al. . | |
| 3,963,685 | 6/1976 | Abrahams . | |
| 3,975,350 | 8/1976 | Hudgin et al. . | |
| 3,982,537 | 9/1976 | Bucalo | 128/260 |
| 3,995,635 | 12/1976 | Higuchi et al. | 128/260 |
| 4,030,499 | 6/1977 | Bucalo | 128/260 |
| 4,056,496 | 11/1977 | Mancini et al. . | |
| 4,064,086 | 12/1977 | Cowsar et al. . | |
| 4,069,307 | 1/1978 | Higuchi et al. | 424/22 |
| 4,081,402 | 3/1978 | Levy et al. . | |
| 4,082,613 | 4/1978 | Thirumalachar et al. . | |
| 4,140,121 | 2/1979 | Kuhl et al. | 128/260 |
| 4,140,122 | 2/1979 | Kuhl et al. | 128/260 |
| 4,164,560 | 8/1979 | Folkman et al. | 128/260 |

OTHER PUBLICATIONS

*Abstracts,* ASAIO, vol. 8, 1979, Annual Meeting 4-2-0-79, Charbray Printers, Inc., p. 63.
*Jour. Nat'l. Cancer Inst.,* vol. 10, No. 2, Oct. 1949, pp. 225-252, Algire et al.
*The Merck Manual,* 12th Ed., 1972, pp. 1186-1203.
*The Merck Index,* 9th Ed., 1976, p. 659.
*Jour. Nat'l. Cancer Inst.,* vol. 15, No. 3, Dec. 1954, pp. 509-517, Prehn et al.
*The Lancet,* Dec. 1977, pp. 1257-1259, Gates et al.
*Nature,* vol. 263, No. 5580; pp. 797-800; 10-28-76.
*J. Biomed. Mater. Res.,* Abrahams et al., vol. 9, pp. 355-366 (1975).
*Polymer News,* vol. 3, No. 1, pp. 11-19, Abrahams et al.; Hydro Med Sciences, Inc., New Brunswick, NJ.
*F-DC Reports,* Apr. 2, 1979, T & G 13.
*J. Biomed. Mater. Res.,* Drobnik et al., vol. 8, pp. 45-51 (1974).
*J. Pharm. Sci.,* Zenter et al., vol. 67, No. 10, Oct. 1978, "Progestin Permeation Through Polymer Membranes II".
*Br. Polym. J.,* Haldon et al., 1972, 4, 491-501.
*Scientific American,* Blackshear, vol. 241, No. 6, Dec. 1979, pp. 66-73.

*Primary Examiner*—C. Fred Rosenbaum
*Attorney, Agent, or Firm*—Fisher, Christen & Sabol

[57] ABSTRACT

Hydrophilic polymeric chambers for encapsulating biologically active tissue and methods for their preparation. The tissue refers to those essential cellular components of a particular organ that is capable of receiving, modifying or secreting hormones. A device comprising such chamber and such tissue is fabricated and implanted in a living body so that said tissue is permitted normal function without being rejected by the host's immunological system. The viability of the tissue in the device is maintained by a correlation of factors including pore size and membrane thickness of the hydrophilic chamber. To maintain the viability of the tissue, the implanted device allows the inflow of essential nutrients and gases, and outflow of metabolites and products while simultaneously excluding the ingress of cellular components of the host's immunological system.

43 Claims, 20 Drawing Figures

POROUS HYDROPHILIC MATERIALS, CHAMBERS THEREFROM, AND DEVICES COMPRISING SUCH CHAMBERS AND BIOLOGICALLY ACTIVE TISSUE AND METHODS OF PREPARATION

BACKGROUND OF THE INVENTION

1. Field of Invention(s)

The inventions relate to novel hydrophilic materials which are useful in the fabrication of novel hydrophilic chambers, to said novel hydrophilic chambers, to novel devices comprised of said hydrophilic chambers containing biologically active tissues, and to novel methods for their preparation and to their uses. In various aspects the inventions relate to the treatment of endocrine deficiencies or hypoendocrine syndromes using said chambers and said devices.

2. Prior Art

Biologically active tissue of an animal or human is subject to various disorders and diseases which result in the under production or non-production of biologically active hormones, secretants and products. Other modes of treatment for such tissue deficiencies include bolus injections, whole organ transplants, and mechanical devices for the delivery of hormones or other physiologically important species. Certain problems and drawbacks are associated with each of these treatments to the disease clinically manifested by the deficient state, e.g., endocrine deficiency or hypoendocrine syndrome.

For normal physiological function, the body has a continuous feedback system which is self-regulating. In addition, many biological species work in a concerted fashion to produce the required effect. The practice of bolus injections ignores this fine balance and current technology is not capable of producing reliable implantable glucose sensors, and there are additional intrinsic reliability problems with any mechanical system.

Whole organ transplantation presents special problems of its own. Normally one must resort to some form of immunosuppression which invariably produces many undesirable side effects. Also, the availability of implantable whole organs is very limited.

To illustrate the potential clinical significance of a device for the implantation of biologically active tissue, a detailed description of one of the most widespread endocrine deficiencies, diabetes, is given. No suitable treatment for diabetes was available until the discovery of insulin in 1921. Insulin treatment prevented death from diabetic coma and controlled overt symptoms of the disease, and was mistakenly believed to be a "cure" for diabetes. The prolonged life span made possible by insulin, however, revealed new complications associated with diabetes, such as blindness, kidney disease and cardiovascular disease.

Efforts to cope with diabetes have failed to prevent the disease from increasing. Few substantial improvements in therapy have occurred since the discovery of insulin more than 50 years ago. There is a need not only to prevent and cure diabetes, but also to develop better methods for treating the disease and its complications, which affect virtually every system of the body.

Added to the physical problems of diabetes are the psychosocial and economic effects on the diabetic patient and his family. Persons with diabetes, faced with the prospect of a lifelong disease, possible blindness, and a decreased life expectancy, are understandably plagued by fear and in need of education and counseling. Because the disease requires daily attention, persons with diabetes need instruction in self-therapy, how to administer their own insulin, how to regulate their diet, how to balance physical activity with diet and insulin, and how to explain their disease to others.

Amelioration of diabetes by implantation of a whole organ has been, in general, unsuccessful. Consequently, there has been increased interest in recent years in transplantation of isolated pancreatic islet cells. Successful amelioration of the diabetic state in experimental diabetic animals by transplantation of islet cells has been demonstrated in recent years. Nevertheless, most of these demonstrations have employed isografts or autografts and, therefore, have circumvented the problem of immunosuppression. Those investigators who have addressed the immunological problem have, in general, resorted either to drug immunosuppression, host irradiation, or encapsulation of the islets in diffusion chambers for immunological protection. Drug immunosuppression and host irradiation, however, have not proved successful in the long run, and their dangerous systemic side effects make them prohibitive for consideration in young diabetics.

Diffusion chambers of cellulosic or polycarbonate materials containing islet cells have been planted in animals. However, the resulting device, e.g., chamber and cells, generally remains effective for limited periods of time because the body encapsulates the device with fibrous material blocking the passage of insulin, nutrients, and/or waste products.

Gates, R. J., et al.: Reversal of Streptozatocin Induced Diabetes In Rats By Intraperitoneal Implantation of Encapsulated Neonatal Rabbit Pancreatic Tissue, (1977) *LANCET II:* 1257–1259, discloses the implantation of diced rabbit neonatal pancreas, encased in Nucleopore chambers (0.4 $\mu$m pore rating), which reversed streptozotocin-induced diabetes in rats. It is reported that no rejection reactions were observed after six weeks.

The literature is replete with studies demonstrating the diffusion of non-protein, low molecular weight species across hydrogel films.

U.S. Pat. No. 4,064,086 discloses hydrogels formed from certain thermoplastic hydrophilic polymers condensed from a spirolactone and a difunctional compound. Formation polymerization can be carried out in the presence of various useful additives. The additive can be a nonreactive biologically active agent, such as, a therapeutic drug. U.S. Pat. No. 4,056,496 discloses a hydrogel prepared from a hydrophilic acrylate monomer. The hydrogels can be impregnated with a solution containing a drug. U.S. Pat. No. 3,577,512 discloses an oral sustained release dosage form composed of a finely divided therapeutically active agent (e.g., a hormone) and a water insoluble hydrophilic acrylate or methacrylate polymer. U.S. Pat. No. 3,896,806 discloses an implant for directed infusion of active substances, such as, a drug. The implant consists of a hollow body with one wall formed by a thin permeable membrane and with a chamber inside the body, which chamber is connected at least by one channel with the outside space. This enables practically undirectional diffusion of the active substance directly to the affected tissue and ability to maintain or arbitrarily change the concentration and type of the active agent.

U.S. Pat. No. 3,975,350 discloses an implantable polyurethane carrier system containing an active agent, such as medicinal agents, enzymes and antioxidants. The carrier system can be a hydrogel which provides a leachable matrix for leaching out the active agent by body fluids. U.S. Pat. No. 3,857,932 discloses an implantable dry composition of a therapeutically active material and a water insoluble hydrophilic acrylate polymer. The active material can be a number of things such as antibiotics, hormones and vitamins. U.S. Pat. No. 3,551,556 discloses a system whereby drugs are released gradually to a living organism after oral ingestion, implantation, or external application to the skin or a mucous membrane through a layer of a non-inorganic, neutral hydrogel of a polymer of ethylene glycol methacrylate or similar monomer cross-linked sufficiently to make the polymer insoluble in all body liquids. The drug may be distributed in the monomer mixture prior to polymerization or enveloped by an outer coating of the hydrogel. The term biologically active substances therein is not extended to biologically active living cells or tissue.

U.S. Pat. No. 3,885,078 discloses preparing a spongy hydrogel made by polymerizing ethylene glycol monomethacrylate (or the like) in the presence of a small amount of a cross-linking agent and more than 60 percent of water. A laminate thereof can be used as a dressing for burn wounds after it has been provided with fine holes (e.g., by means of a sharp brush)—the fine holes allow removal of the exudate, but prevent access to bacteria. U.S. Pat. No. 3,825,458 is based on the same patent application.

U.S. Pat. No. 3,499,862 discloses that sparingly cross-linked polymers reach osmotic equilibrium with water or aqueous liquids at a water content of 40 percent or less. If the polymer contains less than 40 percent water, it will absorb water from an ambient aqueous medium and its volume will increase by swelling.

U.S. Pat. No. 3,767,790 discloses dosages of microorganisms are entrapped in a hydrophilic acrylate or methacrylate to provide controlled release or quick release or to provide a regulated time of contact with an environment on which the microorganisms can act. The disclosure is limited to microorganisms, such as, bacteria, which is stated to be advantageous over the type of scheme where leachable nutrients are entrapped in a polymer. U.S. Pat. No. 3,860,490 is based on a division of such patent.

U.S. Pat. No. 3,963,685 discloses that water-insoluble, methanol-soluble, hydrophilic polymers such as polymers of 2-hydroxyethyl methacrylate can be prepared by limiting the amount of crosslinking agent such as ethylene glycol dimethacrylate to 0.035 weight percent, or less, based on the weight of monomers. The patentee further establishes in a series of experiments that this methanol-solubility characteristic of the polymer is converted to methanol-insolubility by using from 0.05 to 0.088 weight percent crosslinking agent; see Table 5 of U.S. Pat. No. 3,963,685. The patentee neither contemplates the preparation nor does he disclose the novel chambers and novel devices of the inventions contemplated herein. Additionally, data presented herein, particularly Example 8 and SEM photographs (FIGS. 13-16) of patentee's hydrophilic polymer vis-à-vis applicants' hydrophilic polymer, establish significant differences discussed hereinafter to render the applicants' hydrophilic polymers patentable thereover.

Prehn, R. I., et al.: The Diffusion-Chamber Technique Applied To A Study Of the Nature of Homograft Resistance. (1954) *J.N.C.I.* 15:509–517, discloses experiments with tumor cells in an implant in the peritoneal cavity of mice.

Further see U.S. Pat. Nos. 3,428,043, 3,574,826, 3,567,660, 3,641,237, 3,660,071, 3,660,563, 3,670,073, 3,681,089, 3,681,248, 3,689,634, 3,699,089, 3,737,521, 3,765,414, 3,772,215, 3,818,894, 3,861,416, 3,862,452, 3,881,026, 3,982,537, 3,995,635, 4,030,499, 4,069,307, 4,081,402, 4,140,121 and 4,140,122.

Attention is also drawn to the following references:

Abrahams, R. A., et al.: Blood Compatible Coatings of Hydron Hydrophilic Polymers, (1975) *Polymer News* 3: 11–19.

Abrahams, R, A., et al.: Biocompatible Implants for The Sustained Zero-order Release of Narcotic Antiseptic. (1975) *J. Biomed. Mats.* 9: 355–366.

Langer, R., et al.: Polymers For The Sustained Release Of Proteins And Other Macromolecules. (1976) *Nature* Vol. 263, No. 5580: 707–800.

Dsobnik, J., et al.: Diffusion of Antitumor drugs Through Membranes From Hydrophilic Methacrylate Gels. (1974) *J. Biomed. Mater. Res.* 8: 45–51.

Zentner, G. M., et al.: Progestin Permeation Through Polymer Membranes II: Diffusion Studies On Hydrogel Membranes. (1978) *J. Pharm. Sci.* Vol. 67, No. 10: 1352–1355.

Holdon, R. A., et al.: Structure and Permeability of Porous Films of Polyhydroxyethyl Methacrylate. (1972) *Br. Polym. J.* 4: 491–501.

Algire, G. H., et al.: Recent Developments in the Transparent-Chamber Technique as Adapted to the Mouse. (1949) *J.N.C.I.* 10: 225–253.

DESCRIPTION OF THE INVENTIONS

Objects of the inventions are to provide novel hydrophilic materials which are useful in the fabrication of novel hydrophilic chambers, and to the novel hydrophilic chambers therefrom, said materials and said chambers being biologically compatible with body tissue and having a semi-permeable hydrophilic structure, the porosity of which permits the diffusion of small particles therefrom, such as hormones, and which prevents the ingress of large particles therein, such as cells. Another object of this invention is to provide a novel device or article which comprises such materials or chambers and biologically active tissue contained therein. Another object of this invention is to provide such a device or article prepared from a material which is compatible with body tissue and non-toxic thereto and which does not trigger the rejection mechanism of the host. Another object of this invention is to provide such a device made from a material which can be fabricated and/or sealed into various shapes and structures without substantially adversely effecting the properties of the biologically active tissue contained therein. Another object of this invention is to provide a novel process of utilizing such device to treat or alleviate a hypoendocrine syndrome in a host body. Another object of this invention is to provide a novel kit composed of such chamber, such biologically active tissue and assorted pertinent paraphenalia from which such device can be assembled. Other objects and advantages of this invention are set out herein or are obvious herefrom to one ordinarily skilled in the art.

The objects and advantages of the inventions are achieved by the preparation and utilization of the hydrophilic material, of the chamber and of the device.

The broad inventions are directed to novel materials per se, novel chambers per se, novel devices comprised of said materials or chambers therefrom and biologically active tissue, novel processes for the preparation of same, and novel processes for contacting such hydrophilic materials, such chambers, and such devices with the body, e.g., tissue, oral mucosa, skin, and other portions of the animal. The term "biologically active tissue" as used herein refers to those essential viable cellular components of a particular organ that are capable of receiving, modifying, or secreting viable hormones. The novel device containing such tissue can be placed, for example, in a living body. Various characteristics of the novel hydrophilic material and novel chamber therefrom such as pore size, thickness of the membrane, and the like are controlled so that the ultimate device has the capability of preventing both the entry of white blood cells therein and the exit of the contained biological active tissue therefrom while also simultaneously permitting the ingress of nutrients from body fluids therein and the egress of waste products and biological active secretants, e.g., hormones, therefrom. The result is a viable, ongoing source of hormones and/or other secretants from the biologically active tissue imbedded or contained in the novel device which functions on a relatively long-term basis without host body rejection.

In one aspect the invention is directed to novel hydrophilic materials which are in a form useful for fabricating into novel hydrophilic chambers, said materials being characterized by 3-dimensional reticulum-like porosity, water-insolubility, water-swellability, biological inertness, non-toxicity to and compatibility with living tissue, and retention of structural integrity over long periods of time in contact with body fluids. As will become apparent from the working Examples and the accompanying Figures, the novel hydrophilic material (and novel chambers and novel devices fabricated therefrom) are particularly characterized by a relative, substantially uniform maximum porosity or average diameter such that cellular entities, particularly white blood cells, are unable to trigger an immune response or rejection of the chamber or device when it is in contact with living tissue. On the other hand, the geometry of such porosity is generally at least sufficient to permit the egress and ingress of a steroid molecule (taken as a reference point to establish the minimum average diameter of the pore openings). The hydrophilic materials which are most suitable in the practice of the invention are characterized by a reticulum-like, porous structure in which at least about 75%, preferably at least about 90%, of the average diameter of the pores does not exceed about 10 $\mu$ as determined under a scanning electron microscope (SEM), and in which the average diameter of the remaining pores (below about 25%, preferably below about 10%) is generally sufficiently small so as not to cause (or to prevent) an immune rejection when the hydrophilic material containing biologically active tissue therein is in contact with or imbedded in a living tissue environment. In general, the average diameter of such remaining pores is not greater than about 20 $\mu$. Inasmuch as the semi-permeable and channeling characteristics will influence, to a significant degree, porosity dimensions, the aforesaid dimensions of the reticulum-like, porous structure most preferably will be characteristic of hydrophilic membranes of at least about 100 $\mu$ thickness and upwards to about 1000 $\mu$ thickness. Though the invention contemplates a thickness range somewhat outside the aforesaid range, it should be noted that membranes, for example, of about 30 $\mu$ thickness may be quite difficult to fabricate into chambers and devices without causing frequent tears and rips in the fabricated structure. It is within the contemplation of the invention, however, to deposit a coating or film of the hydrophilic material on to a reinforced structure, capsule, etc., to fabricate reinforced chambers and devices. In such instances, the membrane thickness can be substantially less than 100 $\mu$, for instance, about 30 $\mu$ and less. The resulting hydrophilic chambers and devices therefrom are non-immunogenic and thus do not trigger the immune response or rejection and do not promote fibrous encapsulation thereof with tissue by the body which would occlude the pores and thereby obstruct or compromise the transportation of nutrients and/or chemical stimulating factors into the chamber or device and the egress of biological active products, e.g., hormones, and waste products therefrom.

The term "biological active secretant(s)" as used herein refers generally to viable secretants as illustrated by the hormones which are generated or produced by the biologically active viable tissue contained in the novel device.

The novel chamber can be fabricated from the novel hydrophilic material. The novel chamber can take any suitable form, size and shape, as is illustrated in the drawings and examples, e.g., pouch, sheet, capsule, cylinder, spheroid, laminate, and the like. The structure of the hydrophilic material can be a sparingly or lightly crosslinked structure to one possessing a relatively high degree of crosslinking density. In the former, the water-swellability characteristic of the chamber will be generally much greater than would be the case with chambers exhibiting such high crosslinking densities.

The hydrophilic material or chamber therefrom when immersed in water will swell therein until it reaches equilibrium with the liquid environment. Such materials and chambers, depending to a large degree on the materials and techniques used to make the hydrophilic material, can take up as little as 5 weight percent water and upwards to 4000 weight percent water, and higher, based on the weight of the hydrophilic material to form hydrogels. Materials and chambers which possess a water uptake capability of from about 10 to about 2500 weight percent are generally suitable for the uses contemplated herein. Preferably, the water uptake is from about 20 to about 2000 weight percent, and preferably still, from about 25 to 500 weight percent, based on the weight of the material or chamber (dry).

In another aspect, the invention is directed to novel devices containing biologically active tissue in the novel hydrophilic chamber. In these devices the membrane thickness (barrier) is governed, to a realistic degree, by maintaining the proper diffusivity (egress) of the biologically active secretant, e.g., hormone, from the novel device while simultaneously excluding ingress into the device of cellular species responsible for immune rejection, e.g., white blood cells. The term "membrane thickness" of the device as used herein refers to the distance (barrier) separating the biologically active tissue contained in the device from the surface of the device. In the event the device is imbedded in living tissue, the barrier can be considered to be the distance between the host environment and the biological active tissue. As indicated above, the upper limit of the membrane thickness of the novel device allows for the proper diffusivity of the non-cellular entities while preventing ingress of the cellular entities. The device is biologically inert, non-toxic to and compatible with living tissue, and retains its structural integrity over long periods of time in contact with living tissue and body fluids, e.g., several months.

The hydrophilic material from which the novel chamber and novel device are fabricated possesses sufficient structural integrity or mechanical properties to enable the fabricator and/or clinician to construct such chamber and/or device essentially free of physical defects, e.g., holes, tears, etc., during the fabrication and subsequent uses thereof. In general, a suitable hydrophilic material possesses an ultimate strength of about 3 $g/mm^2$ to 200 $g/mm^2$, preferably about 5 $g/mm^2$ to 100 $g/mm^2$, and an initial tear strength of 0.1 g/mm to 20 g/mm, preferably 1 g/mm to 10 g/mm, and a propagation tear strength of 0.5 g/mm to 10 g/mm, preferably 1 g/mm to 5 g/mm as determined by a modification of ASTM D-1938-67, i.e., using a sample specimen of the dimensions 5 cm by 2.5 cm by 1 mm and said specimen being immersed in water and in equilibrium therewith. Hydrophilic materials exhibiting mechanical properties outside the aforesaid illustrative ranges are also contemplated within the scope of the invention since the ultimate properties will depend, to a significant degree, on the source of the polymer, concentration and type of crosslinking agent, if any, employed in the preparation of the polymer, and other factors.

In another embodiment the invention is directed to the novel device comprising a hydrophilic chamber and biologically active tissue, which is incorporated into or in juxtaposition with live tissue or a living body to treat, eliminate or alleviate a disease generally caused by tissue deficiency or malfunction. Illustrative examples of such biologically active tissue, and a brief description of the clinical manifesting resulting from the tissue deficiency, follow:

| Tissue | Function |
| --- | --- |
| 1. Pancreas | The endocrine tissue of the pancreas functions to elaborate, store and secrete insulin and glucagon. These hormones affect carbohydrate, protein and fat metabolism. Hypoglycemia and hyperglycemia (diabetes) may be treated with devices of this invention containing particulated pancreatic tissue. |
| 2. Thyroid | The function of the thyroid is to elaborate, store and secrete hormones (primarily thyroid hormone and calcitonin) that are concerned principally with the regulation of the metabolic rate. Primary hypothyroidism or cretinism (in children) may be treated with devices of this invention containing particulated thyroid tissue. |
| 3. Parathyroid | This gland produces parathyroid hormone in response to low blood calcium concentration. It is important in the regulation of calcium and phosphate levels. Hypoparathyroidism, resulting in decreased calcium concentration, may be treated with devices of this invention containing particulated parathyroid tissue. |
| 4. Adrenal Gland | The adrenal gland produces several products required for salt management, fluid and electrolyte balance, carbohydrate, protein and fat metabolism, etc. Addision's disease resulting from lack of adrenal function, may be ameliorated with devices of this invention containg particulated |

-continued

| Tissue | Function |
| --- | --- |
| | adrenal tissue. |
| 5. Gonads, Testicular and Ovarian Tissue | The gonads secrete hormones necessary for proper sexual development and function. For example, the devices of this invention containing particulated testicular tissue may be used to treat eunuchism (testicular deficiency) by providing testosterone. Estrogens and other hormones produced by the ovary can similarly be replaced clinically in deficiency states (i.e., menopause). |
| 6. Thymus | The thymus gland is essential for the establishment and maintenance of immunologic competence. It has been suggested that the thymus is the source of a blood-borne factor which induces the differentiation of lymphoid precursor cells rendering them capable of participating in immune reactions. Certain immune deficiencies may be alleviated by the device of this invention containg particulated thymus tissue. |
| 7. Liver | The liver has many functions including glucose, fat and protein metabolism, degradation of drug cell waste products, formation of bile, proteins, albumin, blood clotting factors, etc. By the practice of certain aspects of the invention funtions may be restored in patients with, for example, liver failure resulting from various causes (tumor, hepatitis, Wilsons disease, infection, intoxication, hemochromatosis etc.). |

Other biological active tissues, such as kidney and pituitary, can be contained in the novel hydrophilic device. However, their functional capacity depends upon their neural and vascular connections encountered in its normal anatomical site.

The biologically active tissue is desirably used in particulate form. The actual particle size and the quantity of biologically active tissue in the novel device will depend, to a significant degree, on a correlation of various factors such as the chemical composition of the hydrophilic chamber, the construction of the device, the biological active tissue of choice, the disease to be treated, ameliorated, or controlled, the environment of the device including the nutrients available for generating or promoting the formation of biologically active secretants, and other considerations. The novel device will contain an amount of biologically active tissue at least sufficient to effect the desired result, i.e., treat, ameloriate, and/or control the targeted disease. In the event the contemplated device contains an insufficient amount of biologically active tissue for the intended purpose, the skilled and experienced clinician can make the necessary adjustment(s).

The hydrophilic material which will form the chamber (and device) can be prepared from a wide variety of materials. For example, 3-dimensional hydrophilic polymeric products ranging from a lightly or sparingly crosslinked network to a relatively highly crosslinked system are useful in the practice of the invention(s). Such products are carefully prepared by controlled polymerization techniques which utilize a monomeric feed comprising at least one of the following illustrative monomers: monoesters of an acrylic acid or methacrylic acid with an alcohol having an esterifiable hydroxyl group and at least one additional hydroxyl group such as the mono- and polyalkylene glycol monoesters of methacrylic acid and acrylic acid, e.g., ethylene glycol monoethacrylate, ethylene glycol monoacrylate, diethylene glycol monomethacrylate, diethylene glycol monoacrylate, propylene glycol monomethlate, dipropylene glycol monoacrylate, and the like; the N-alkyl and N,N-dialkyl substituted acrylamides and methacrylamides such as N-methylacrylamide, N,N-dimethylacrylamide, N-methylmethacrylamide, N,N-dimethylmethacrylamide, and the like; N-vinylpyrrolidone; the alkyl substituted N-vinyl pyrrolidones, e.g., methyl-substituted N-vinylpyrrolidones; the vicinal epoxyalkyl 2-alkenoates, e.g., glycidyl methacrylate and glycidyl acrylate; and others known to the art.

The polymerization reaction is conducted in the presence of a crosslinking agent in the monomeric feed as illustrated by ethylene glycol diacrylate, ethylene glycol dimethacrylate, 1,4-butylene dimethacrylate, diethylene glycol dimethacrylate, propylene glycol dimethacrylate, diethylene glycol diacrylate, dipropylene glycol diacrylate, divinylbenzene, N,N'-methylene-bis-acrylamide; the di-, tri-, and higher polyesters of acrylic acid and methacrylic acid with the following polyols: triethanolamine, glycerol, pentaerythritol, 1,1,1-trimethylolpropane, mannitol, sorbitol, and the like.

The monomer(s) of choice, the crosslinking agent of choice, the diluent(s) of choice, the ratio of the diluent(s) to monomer(s), and other factors will influence the amount of crosslinking agent to be employed in order to obtain novel hydrophilic materials having the contemplated effective pore size. We have observed that a polymerization system comprising, as the monomers, 2-hydroxyethyl methacrylate which contained 0.12 weight percent ethylene glycol dimethacrylate as the crosslinking agent and distilled water (75 weight percent water/25 weight percent monomers) and 0.5 weight percent redox initiators (based on weight of monomer) resulted in hydrophilic polymeric membranes of about 200 $\mu$m thickness having a substantially uniform, reticulum-like porosity of average pore diameter of about 5 $\mu$m to about 10 $\mu$m; see FIG. 13. Duplicating the aforesaid experiment using 0.17 weight percent in lieu of 0.12 weight percent of the crosslinking agent gave similar results; see FIG. 14. On the other hand, we have observed that the use of less than 0.02 weight percent and 0.08 weight percent of ethylene glycol dimethacrylate, in lieu of 0.12 weight percent or 0.17 weight percent ethylene glycol dimethacrylate, in the same polymerization system under the same conditions resulted in polymeric films characterized by bimodal pore size distributions, that is, pores of two type sizes—small (less than about 10 $\mu$m in diameter) and relatively large (about 35 $\mu$m in diameter) for the polymerization system employing 0.02 weight percent crosslinking agent, and less than about 10 $\mu$m in diameter and about 65 $\mu$m in diameter for the polymerization system using 0.08 weight percent crosslinking agent; see FIGS. 15 and 16. Such polymers are not desirable in the practice of the invention since there exists a high degree of probability of invasion of the host's white cells into the novel chamber or novel device, and further, the permeability characteristic of such a film (membrane) is generally more difficult to control than is the case with a substantially uniform porous material. Depending on the correlation of variables, i.e., choice of monomers and diluent(s), diluent/diluent ratio, diluent(s)/monomer ratio, and the like, an amount greater than 0.1 weight percent of crosslinking agent such as ethylene glycol dimethacrylate based on the weight of monomer such as hydroxyalkyl methacrylate, e.g., 2-hydroxyethyl methacrylate, has been observed to give hydrophilic polymeric films or membranes characterized by porosity contemplated by the invention. One skilled in the art can determine the upper limit of crosslinking agent to be used in the polymerization system. For a system containing 2-hydroxyethyl methacrylate, ethylene glycol dimethacrylate, and water (using 75 weight percent water/25 weight percent monomers), an upper limit of about 0.5 weight percent appears to be suitable in the practice of the invention. It is to be understood that different systems may cause the upper limit to vary and to exceed the aforesaid value.

Preferred monomeric mixtures comprise at least one alkylene glycol monoester of methacrylic acid, especially ethylene glycol monomethacrylate, and at least one crosslinking monomer such as the alkylene glycol diester of methacrylic acid, especially ethylene glycol dimethacrylate. Such preferred mixtures may contain other polymerizable monomers, desirably in minor amounts such as N-vinylpyrrolidone, glycidyl methacrylate, acrylamide, N-methacrylamide, diethylene glycol monomethacrylate, and others illustrated above and known to the art.

The polymerization reaction is carried out in the presence of a controlled quantity of a liquid reaction medium comprising, as a diluent, water with/without a normally liquid organic vehicle, said water and said organic vehicle, if present, being miscible with each other, said diluent and the monomer mixture being miscible, and said diluent and the resulting polymeric products being immiscible. The organic vehicle desirably does not exceed about 40 weight percent of the diluent.

The diluent employed in the novel process is an amount not exceeding that which can be completely sorbed in the resulting polymeric products at the completion of the reaction. Desirably, the ratio (by weight) of diluent to monomer(s) is from 6:5 to 5:1, preferably from 3:2 to 4:1, and most preferably from 2:1 to 4:1. The resulting hydrophilic materials can be fabricated into hydrogel chambers having the proper effective pore size, good mechanical strength and integrity which in turn can be fabricated into novel devices comprising biologically active tissue.

The normally liquid organic vehicles comprising the water/organic diluent mixture include (in addition to water) water-soluble lower aliphatic monohydric alcohols as well as polyhydric alcohols, e.g., methanol, ethanol, butanol, glycol, glycerol, and dioxane.

Examples of catalyst useful in the polymerization reaction include 1,3-bis-(t-butylperoxyisopropyl)benzene, succinic acid peroxide, bis(1-hydroxycyclohexyl)-peroxide, t-butyl-peroctoate, benzyol peroxide, isopropyl percarbonate, methyl ethyl ketone peroxide, cumene hydroperoxide and dicumyl peroxide. Another group of catalysts useful mainly for low temperature polymerization include redox systems such as potassium persulfate-riboflavin, potassium persulfate-sodium bisulfite and hydrogen peroxide-divalent iron. Also, photoinitiation via such catalysts, such as, benzoin methyl ether, uranyl nitrate and sodium p-toluene sulphinate, can be employed. Various compounds such as N,N,N',N-tetramethylethylenediamine can be used to accelerate the effect of the catalysts. Any suitable catalyst(s) and accelerator(s) can be used to catalyze the polymerization.

Irradiation, e.g., by ultraviolet light or gamma rays, photopolymerization, and the like, can also be employed to initiate and/or catalyze the polymerization reaction and/or to crosslink the resulting polymeric product.

The polymerization reaction can be conducted over a wide temperature range, e.g., 0° C., to 100° C., for a period of time sufficient to produce the desired polymeric products, e.g., about one hour, or less, and upwards to 24 hours, and more. Thereafter, the resulting polymeric products can be purified by conventional technique known in the hydrogel art, e.g., leaching in water and eventual storing in physiological solution, if desired.

Polymerization conditions should not be used which substantially destroy or damage the biologically active tissue where contained in the polymerization reaction medium.

When a sheet-like chamber is needed to prepare the ultimate device, the sheet-like chamber can be fabricated by any suitable method. For example, the resulting hydrogel bulk can be cut or sliced to form such sheet-like or membrane-type chambers.

The novel chambers in desired forms or shapes can be fabricated by various techniques. If a composite or laminate or a membrane and/or other reinforced sheet-like chamber is desired, then a reinforcing structure in the shape of a sheet, laminate, composite, mesh, etc., can be immersed in or coated with the polymerization mixture, prepolymer, or casting syrup, and then the polymerization reaction can be taken to completion to produce the hydrophilic chamber containing such reinforcing structure.

The following is an illustrative list of commercially available semi-permeable support materials which can be used to reinforce the novel hydrophilic chambers and devices therefrom.

Figure 17:
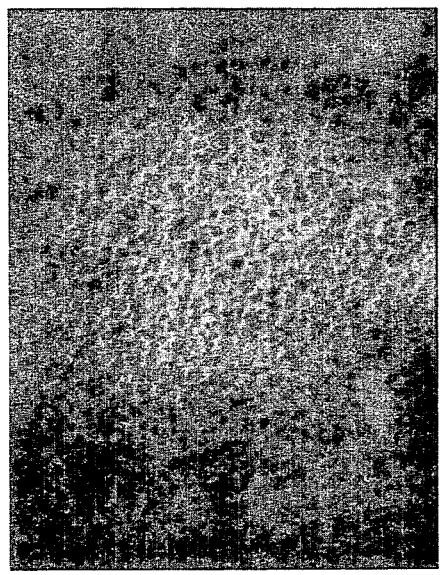
Figure 18:
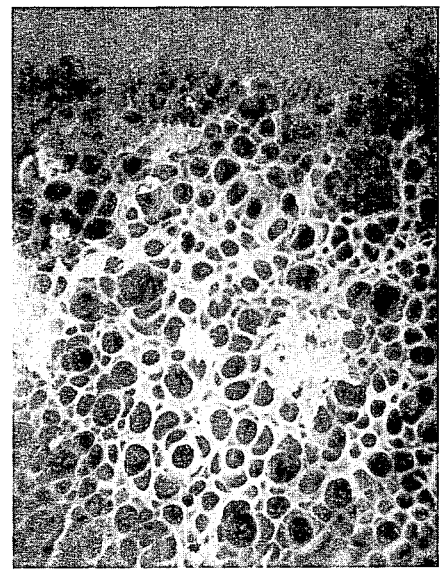
Figure 19:
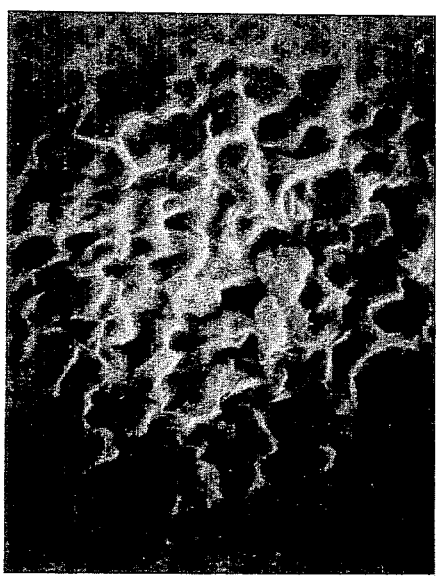
Figure 20:
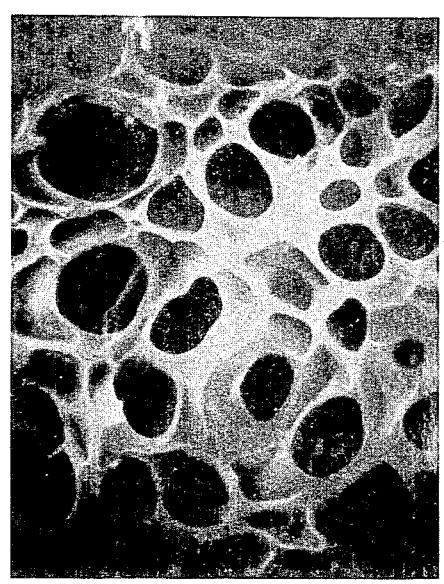

FIGS. 13–20 are photographs of novel hydrophilic material in the form of a film about 0.3 mm thick. The photographs are taken with a scanning electron microscope (SEM), 300 magnification (FIGS. 13–18) or 1,000 magnification (FIGS. 19–20). In FIGS. 13–16, the films are hydrated in distilled water to osmotic equlibrium, then frozen over dry ice, and thereafter allowed to "sublime" until its water content is lost while retaining the porous structure of the hydrophilic material. The photographs of FIGS. 13–16 are top views of films whereas the photographs of FIGS. 17–20 are cross-sectional views taken along the 0.3 mm thickness.

Figure 13:
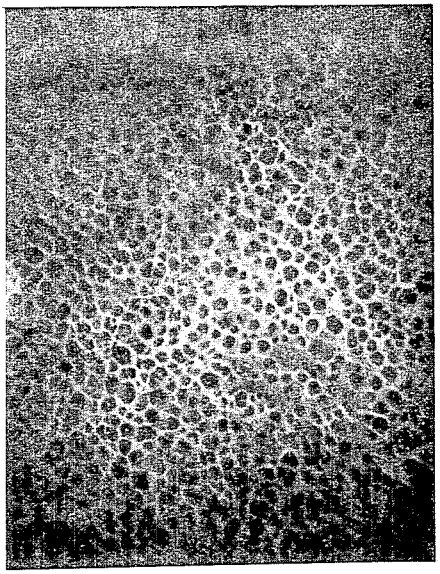

The hydrophilic material photographed in FIG. 13 is obtained by using 0.12 weight percent of crosslinking

| Trade Name | Shape | Composition | Pore Size[1] | Pore Type | Thickness |
|---|---|---|---|---|---|
| Nucleopore* (family of membranes) | sheets | polycarbonate | 0.01 to 12 m dia. | cylindrical | 5 or 10 μm |
| Celgard* (family of membranes) | sheets | polypropylene | 1.02 × 0.2 μm dia. and 0.09 × 0.2 μm dia. | oblong slightly tortuous channel | 25 μm |
| Millipore* (family of membranes) | sheets | cellulose and cellulose derivatives, PFTE, PVC | 0.025 to 10 μm dia. | tortuous | 90 to 170 μm |
| Dacron | fabric | polyester | | open mesh | 5 to 1000 μm |

Figure 1:
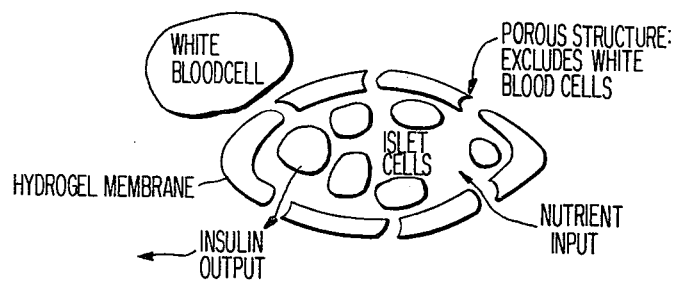

*Well-known trademarks
Note:
μm = μ = micron = micrometer
[1] Ranges express the diameter in μm FIG. 1 represents an exaggerated sectional view of a novel hydrogel device in an environment of living tissue in which the permeability characteristics are such as to allow the inflow of needed nutrients and glucose, and outflow of insulin, while blocking entry of much larger white blood cells which would otherwise recognize the "foreign" islet cells and cause rejection.

Figure 2:
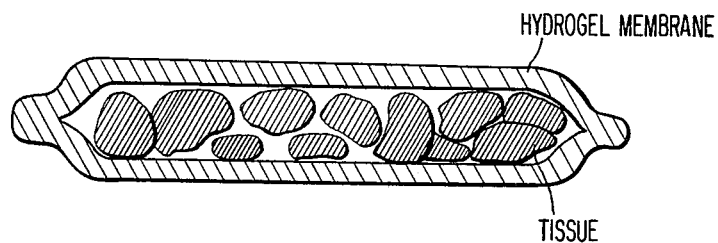

FIG. 2 is an exaggerated sectional view of a novel device in accordance with Examples 1 and 2.

Figure 3:
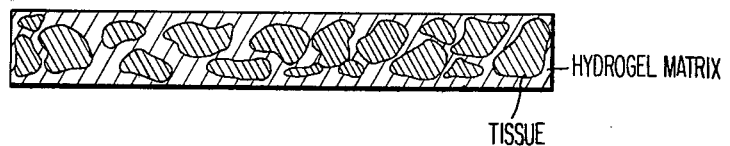

FIG. 3 is an exaggerated sectional view of a novel device in accordance with Example 3(b).

Figure 4:
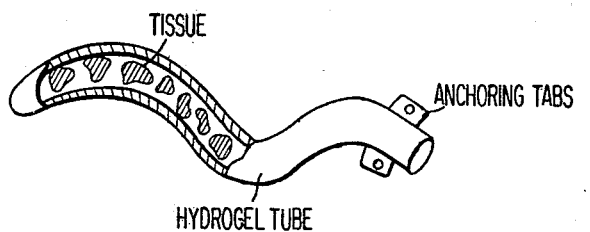

FIG. 4 is an exaggerated partial sectional view of a novel device in accordance with Example 3(b).

agent; see Example 8(a).

Figure 14:
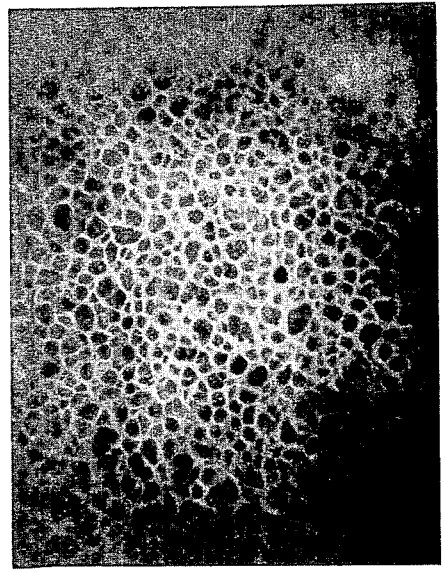

The hydrophilic material photographed in FIG. 14 is obtained by using 0.17 weight percent of crosslinking agent; see Example 8(b).

Figure 15:

The hydrophilic material photographed in FIG. 15 is obtained by using less than 0.02 weight percent of crosslinking agent; see Example 8(c).

Figure 16:
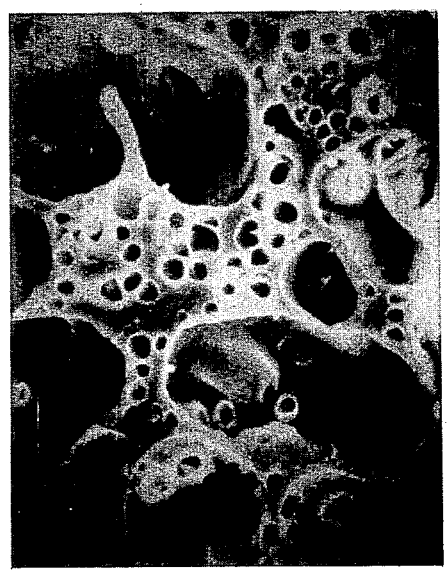

The hydrophilic material photographed in FIG. 16 is obtained by using 0.08 weight percent of crosslinking agent; see Example 8(d).

FIG. 17 is a SEM photograph (300X) of the dehydrated hydrophilic material of FIG. 13; see Example 8(e).

FIG. 18 is a SEM photograph (300X) of the hydrophilic material of FIG. 13 taken after it has been dehydrated and then rehydrated; see Example 8(f).

FIG. 19 is a SEM photograph (1000X) of the dehydrated hydrophilic material of FIG. 13; see Example 8(g).

FIG. 20 is a SEM photograph (1000X) of the hydrophilic material of FIG. 13 taken after it has been dehydrated and then rehydrated; see Example 8(h).

EXAMPLE 1

A hydrophilic chamber in the shape of a pouch is constructed by first preparing sheets of hydrophilic polymer (hydrogel). A glass mold is prepared by applying 0.3 mm strip of Teflon coated adhesive aluminum to three sides of the periphery of one glass plate, to which is clamped a second glass plate. The plate is placed in a vertical position with the non-gasketed edge facing upward.

A 40 g mixture of 2-hydroxyethyl methacrylate monomer containing 0.12 percent by weight of the crosslinking agent ethylene glycol dimethacrylate is degassed under vacuum for about 30 minutes. Two 60 g quantities of distilled water were weighed into separate beakers and degassed for 30 minutes. The degassed water is brought to atmospheric pressure and 0.1 g of ammonium persulfate is dissolved in one beaker (being careful not to introduce air). To the second beaker containing 60 g of degassed water 0.1 g of sodium metabisulfite is added and likewise dissolved. The monomeric mixture and water solutions are mixed (being careful to minimize the introduction of air). Immediately following mixing, the resulting solution is aspirated into a 5 cc syringe. A 30 gauge needle is attached to the syringe and the solution injected into the mold. The film is allowed to polymerize at room temperature for a minimum of two hours before dismantling the mold and removing the film. The film is placed overnight in an excess of distilled water (minimum ratio 1000:1, $H_2O$: film) thus attaining osmotic equilibrium therewith while unreacted monomer and impurities are thereby removed. The film, about 0.3 mm thickness, is cut into several pieces (2 cm by 2.5 cm). Two such pieces are surface dried by blotting with absorbent paper (Kimwipe). A 0.8 cm by 2.5 cm Teflon coated aluminum spacer is placed on one piece. Three edges are sealed (adhesive).*

*Adhesive is prepared by mixing equal quantities of Solution A and Solution B. Solution A contains 60 g HEMA, 0.6 g benzoyl peroxide, and 4.2 g Aerosil ®. Solution B contains 36 g HEMA, 24 g diacetin, 4.2 g Aerosil ® and 0.6 g diamino accelerator.

The hydrogel chamber in the form of a pouch (sealed on three sides) is sterilized by radiation. Prior to implantation, the chamber is filled by injecting freshly collected, viable, neonatal rat or rabbit pancreas cells through a tapered catheter into the open end of the pouch. The open end of the pouch is then sealed (cyanoacrylate adhesive). See FIG. 2. The completely sealed pouch (device) is implanted by suturing with non-reactive stay sutures to the peritoneal cavity (rat). Examples of other implantation sites are the abdominal cavity, subcutaneous tissue (under the skin), intra-arterial (lumen of a large artery), intramuscular (in the plane of muscle), intra hepatic (in the liver), renal (under the renal corpuscle) and bone marrow cavity. The incision is closed with sutures and the skin is sprayed with a topical antiseptic.

EXAMPLE 2

A hydrophilic chamber (hydrogel) is prepared by casting in molds a monomer mixture. The mixture is formulated as follows:

A 40 g mixture of 2-hydroxyethyl methacrylate monomer containing 0.2 percent by weight of the crosslinking agent, ethylene glycol dimethacrylate, is degassed under vacuum for about 30 minutes. Two 60 g quantities of a mixture of distilled water and methanol (3:1, v/v) are weighed into separate beakers and degassed for 30 minutes. The degassed water/methanol solutions are brought to atmospheric pressure and 0.1 g of ammonium persulfate is dissolved in one beaker (being careful not to introduce air) and to the second beaker is added 0.1 g of sodium metabisulfite and likewise dissolved therein. The monomer and water methanol solutions are then mixed (being careful to minimize the introduction of air). The resulting solution is poured into the mold, which is then closed. The solution is allowed to polymerize at room temperature for a minimum of two hours before dismantling the mold and removing the hydrophilic chamber (hydrogel). The resulting chamber is placed in an excess of distilled water (minimum ratio 1000:1, $H_2O$: chamber weight) overnight to remove any impurities, especially unreacted monomer and catalyst residue. As described in Example 1, the chamber is sterilized, filled with cells, sealed and implanted. See FIG. 2.

EXAMPLE 3

(a) Viable pancreatic cells imbedded in a novel hydrogel to form a novel monolithic device is prepared as follows. Said cells are first dispersed in the polymerization mixture comprising 4 g of HEMA monomer containing 0.12 percent by weight of the crosslinking agent ethylene glycol dimethacrylate, and 12 g of a mixture of distilled water and methanol (2:1, v/v) containing 0.01 g of dissolved ammonium persulfate and 0.01 g of sodium metabisulfite. The polymerization is carried out at about 0° C., in a mold. The resulting device is stored in a biological medium compatible with the imbedded tissue.

(b) Devices having the shapes shown in FIGS. 3 and 4 can be prepared according to the procedure of Example 3(a).

EXAMPLE 4

Figure 5:
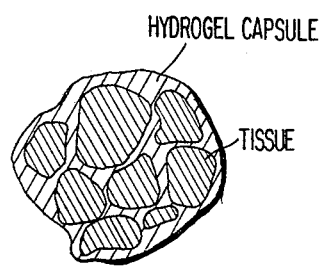
FIG. 5 is an exaggerated sectional view of a novel microencapsulated device in accordance with Example 4.

The device described in Example 3 is quickly frozen (e.g., below 0° C.) and finely ground employing conventional grinding techniques at low temperature. This processing of the device produces a particulated or microencapsulated system (see FIG. 5). The resulting particulated device is suspended in a suitable liquid (e.g., water) and the suspension filtered so as to collect a fraction in the size range of 25 $\mu m$ to 100 $\mu m$ diameter particles. The particles are introduced into a living body via a syringe.

EXAMPLE 5

A hydrophilic chamber similar to that described in Example 1 (or 2) is permanently fitted with a conduit or small I.D. tube (percutaneous catheter) through which viable pancreatic cells are introduced therein. The chamber is also fitted with a second conduit (percutaneous catheter) for the removal of the cells. Once the chamber is implanted, the tube is anchored (by means of the anchoring tube) to the integument or some such part of the body so that cells can be introduced to the chamber ex vivo. This technique permits the recharging of an implanted chamber or device with viable cells without removal of the same from the body. See FIG. 7.

Figure 6:
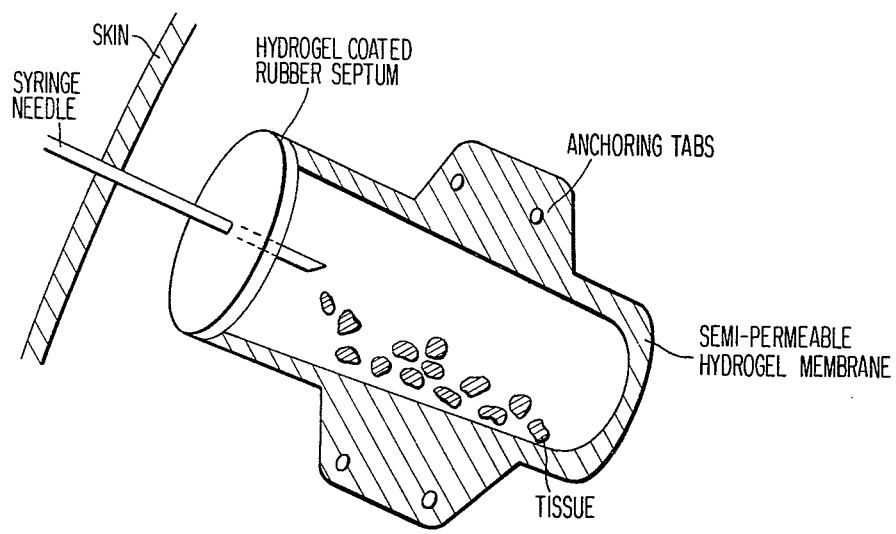
FIGS. 6 and 7 are partial cutaway views of novel devices in accordance with Example 5.
Figure 7:
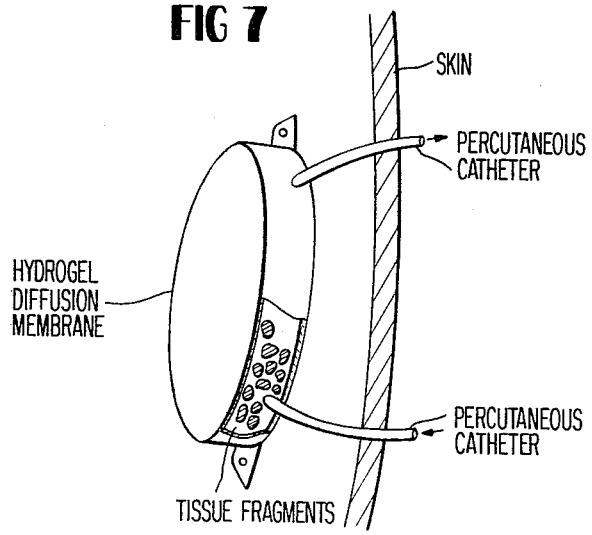

FIG. 6 shows an anchored, rechargeable hydrogel device which is similar in new features to the device of FIG. 7. The chamber can be emptied and refilled transcutaneously using a syringe. The chamber is equipped with a rubber septum, which is hydrogel coated. The syringe needle penetrates the rubber septum, which is sealed by the hydrogel coating when the needle is removed.

EXAMPLE 6

A number of chambers are prepared by the method of Example 1 and illustrated in FIG. 2. In this Example, the diluent is water; otherwise, the procedure is the same as that employed in Example 1.

Twelve of the chambers are filled with neonatal rabbit pancreas tissue (ground up) and each is surgically implanted in a Lewis rat (diabetic) to the peritoneal cavity (by sutures). This is termed Group A. Eleven of the chambers are filled with neonatal rat pancreas tissue (ground up) and each is surgically implanted in a Lewis rat (diabetic) to the peritoneal cavity (by sutures). This is termed Group B. Ten of the chambers (empty) are each surgically implanted in a Lewis rat (diabetic) to the peritoneal cavity (by sutures). This is termed Group C and is the control group.

Some of the test results are set out in the following table:

| Group | Total No. Implanted of Animals | Recipient | Donor (Islet Source) | Total No. Living |
|---|---|---|---|---|
| A | 12 | Rat | Rabbit | 9 (after 35 days) |
| B | 11 | Rat | Rat | 7 (after 35 days) |
| C | 10 | Rat | (none-empty) | 5 (after 35 days) |

(In addition 5 other rats which are not made diabetic and had no implants were tested.)

Figure 8:
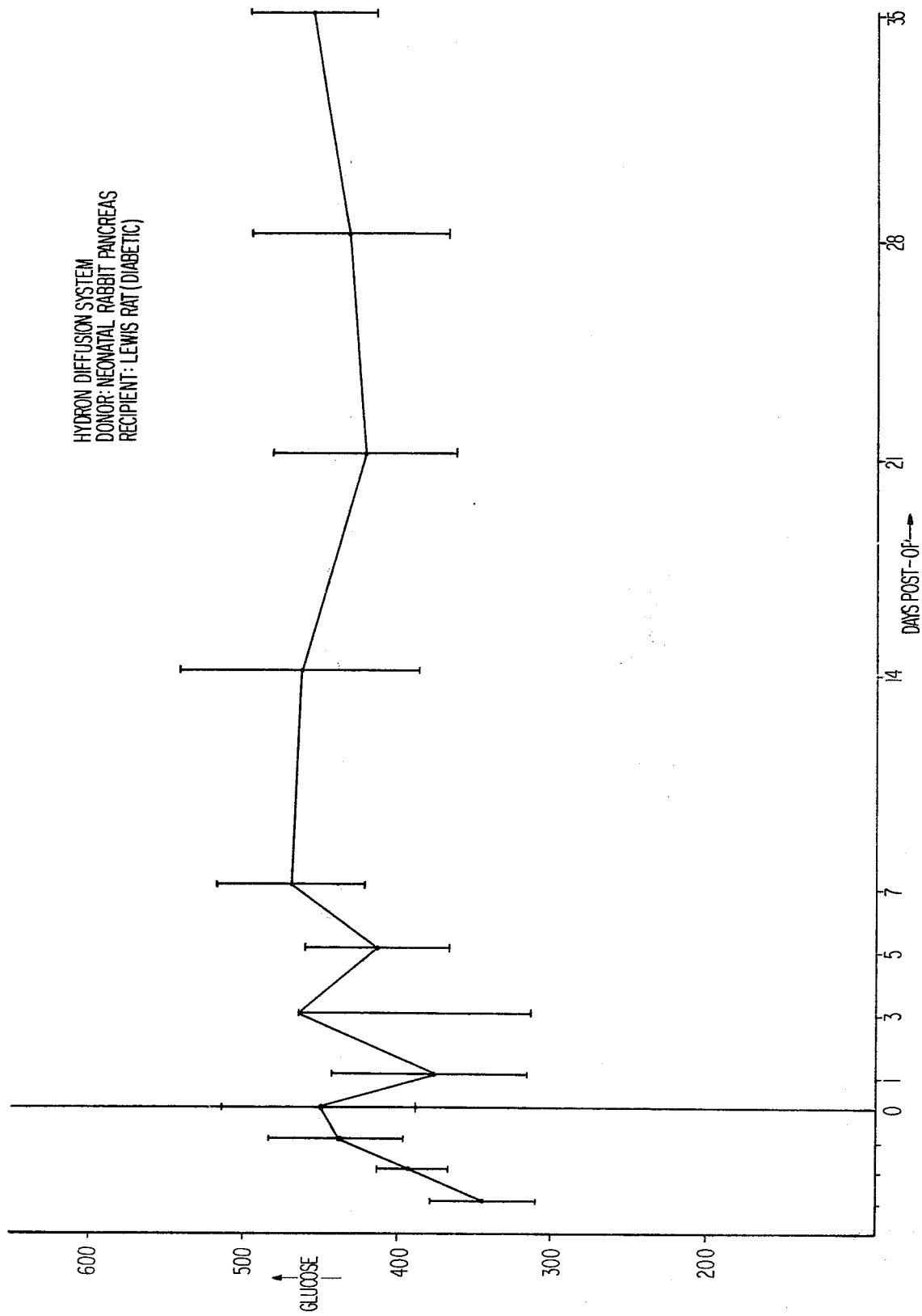
FIGS. 8 and 9 represent graphs obtained by plotting the blood glucose levels (mg/100 ml)/time (days) coordinates of diabetic Lewis rats which have surgically implanted to their peritoneal cavity a novel device containing particulated neonatal rabbit pancreatic tissue; see Example 6.
Figure 9:
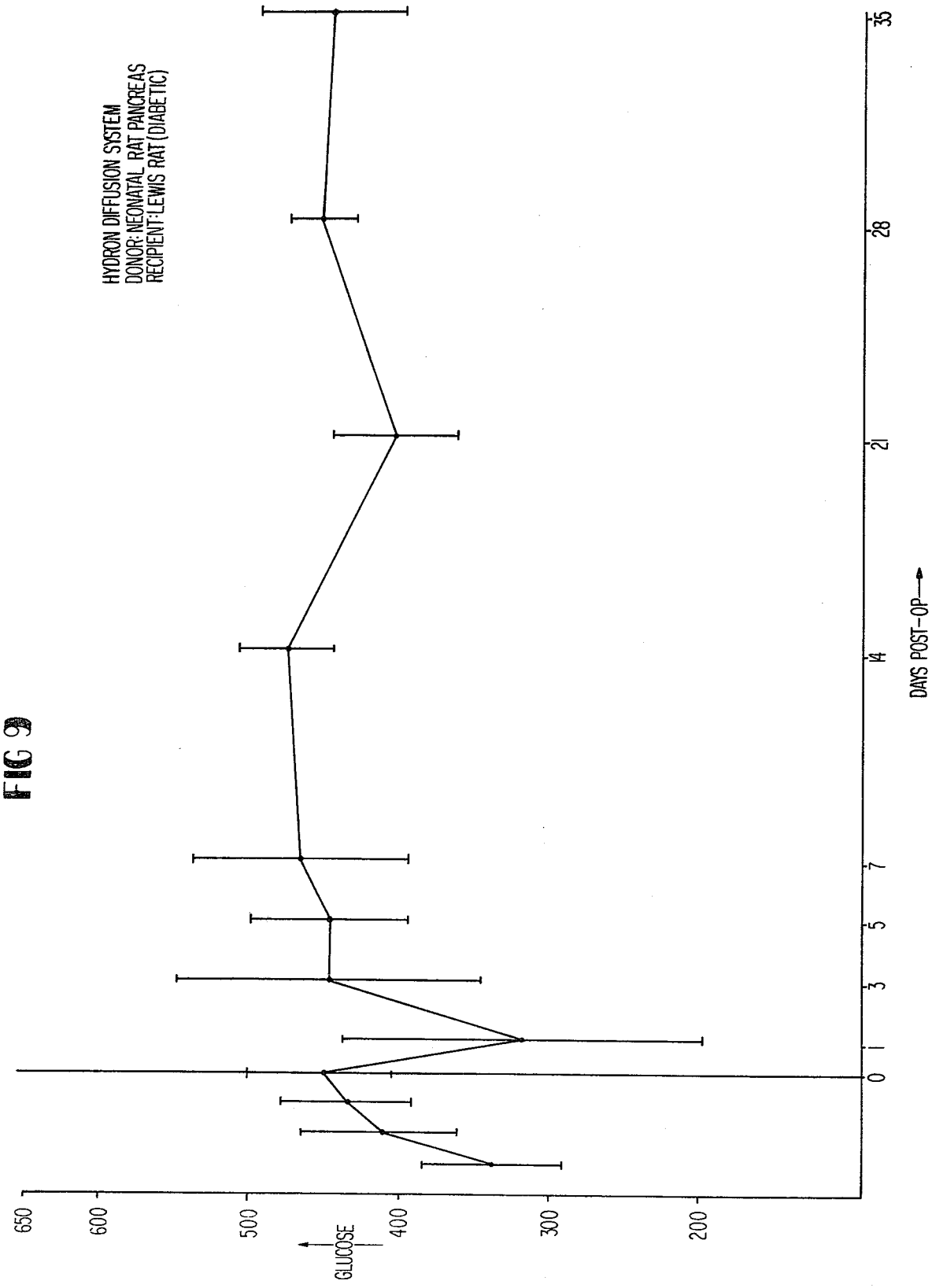
Figure 10:
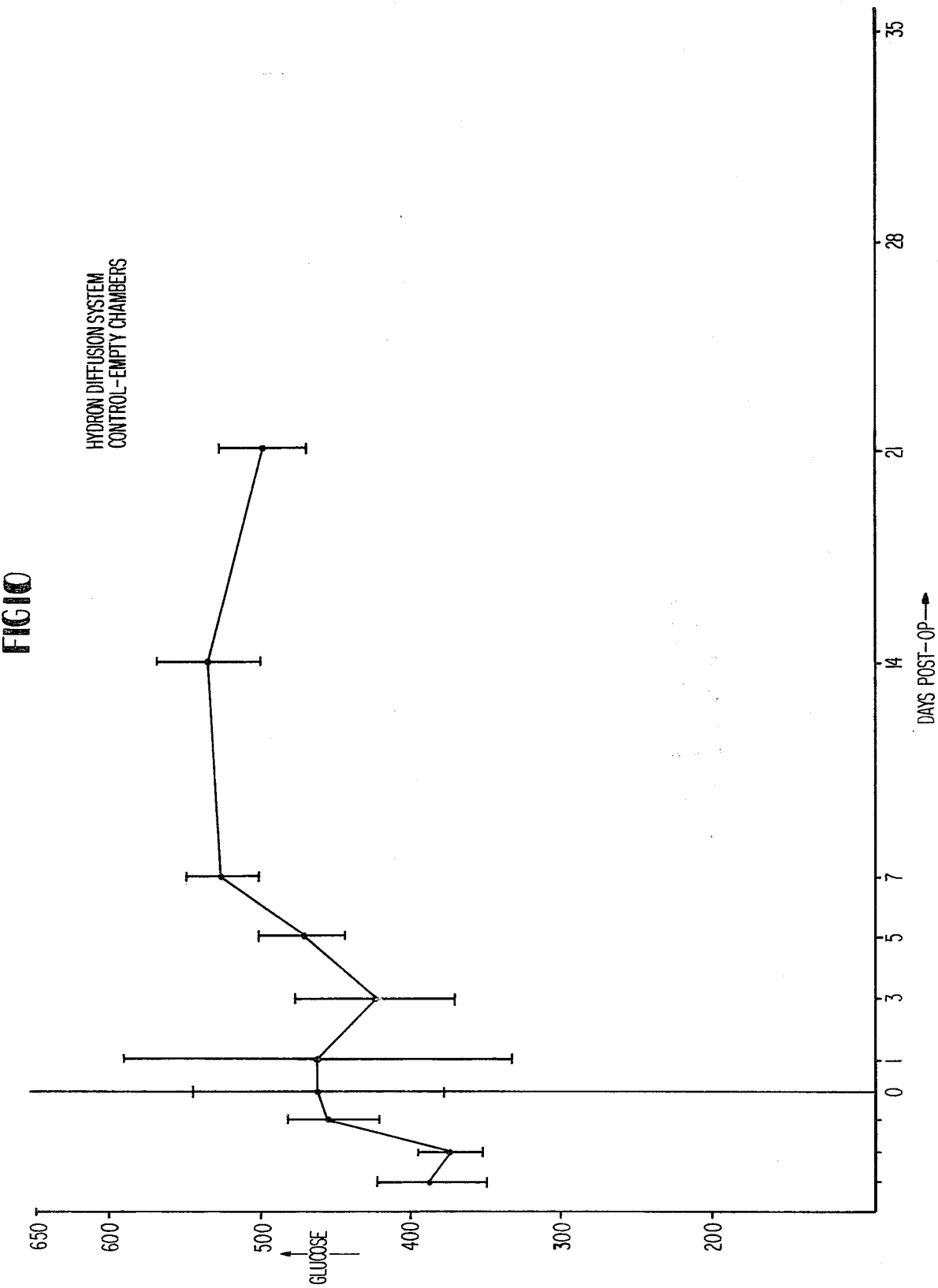
FIG. 10 represents the graph obtained by plotting the blood glucose levels (mg/100 ml)/time (days) coordinates of diabetic Lewis rats which have surgically implanted to their peritoneal cavity a novel chamber per se (the control), i.e., not containing any particulate biologically active tissue; see Example 6.

Blood glucose levels are obtained on day 0 (day of implantation) and then on days 1, 3, 7, 14, 21, etc., post-op. The results are set out in FIG. 8 for Group A, in FIG. 9 for Group B and in FIG. 10 for Group C. There is slight but significant improvement in the average blood glucose level of both study groups receiving devices filled with islets (i.e. Groups A and B compared to the control Group C which received empty devices). In addition, the study Groups A and B appear to be in slightly better condition and experience a decreased mortality rate.

Example 6 is abstracted in Abstracts, Volume 8, 25th Annual meeting, published by ASAIO National Office, P.O. Box 777, Boca Raton, Fla. 33432. The abstracted articles are entitled New Hydrogels For Encapsulation of Pancreatic Islet Cells, by G. F. Klomp, S. H. Ronel, and W. H. Dobelle, and A New Pancreas Chopper For Islet Cell Isolation, by H. Hashiguchi, G. F. Klomp, and W. H. Dobelle.

EXAMPLE 7

The hydrophilic polymeric membranes are prepared by the method of Example 6.

Figure 11:
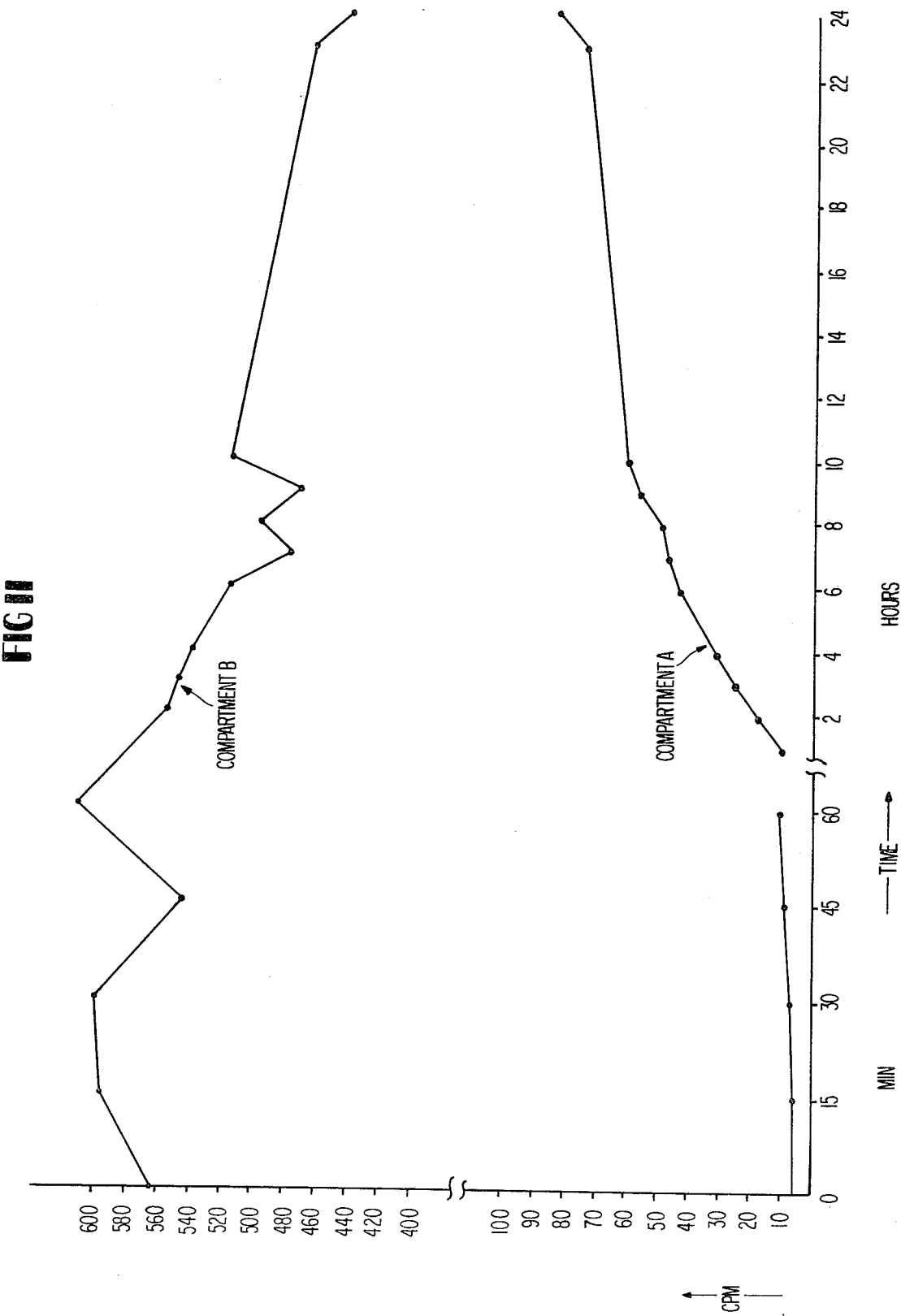
FIG. 11 represents the graph obtained by plotting the $^{125}$I-insulin/time (hours) coordinates of a membrane diffusion study; see Example 7.

A membrane diffusion study is set up, with one of the membranes dividing the container into compartment A and compartment B. Both compartments are initially filled with water at about 30° C. 0.2 cc of $^{125}I$-insulin is added to compartment B at time zero. (The insulin concentration is approximately 4 $\mu$Units/CC.) 0.1 cc aliquots are collected from compartment B at the times indicated in FIG. 11. The diffusion of the $^{125}I$-insulin through the membrane is presented in graph form in FIG. 11.

Figure 12:
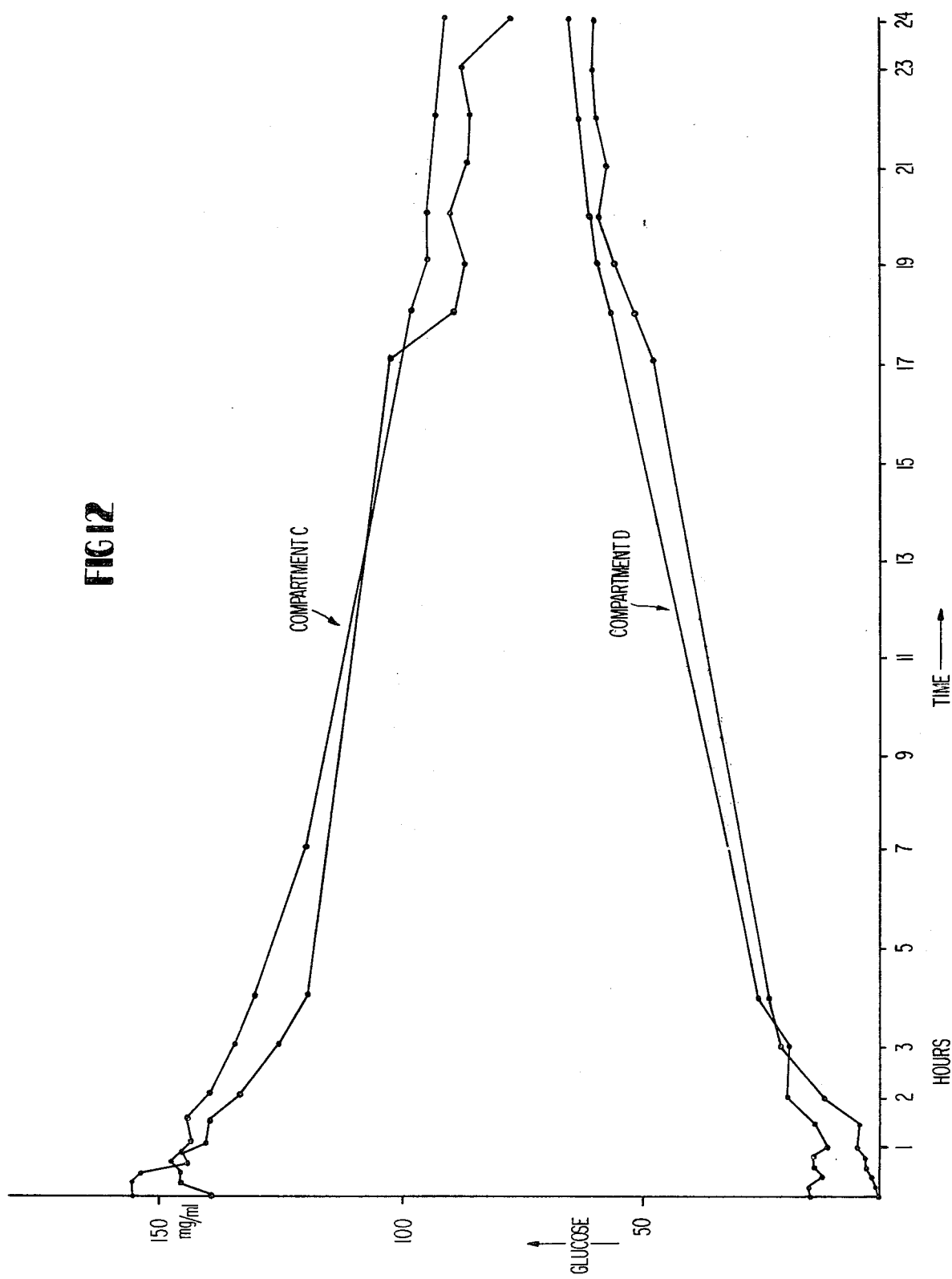
FIG. 12 represents the graph obtained by plotting glucose (mg/ml)/time (hours) coordinates of a membrane diffusion study; see Example 7.

Another membrane study is set up, with one of the membranes dividing a container into compartment C and compartment D. Both compartments are initially filled with water and compartment C is filled with glucose at a concentration of 150 mg percent. 0.02 ml. aliquots are collected from compartment D at the times indicated in FIG. 12. The diffusion of glucose through the membrane is presented in graph form in FIG. 12.

What is claimed is:

1. A synthetic, hydrophilic, polymeric material of a polymer of at least one monomer from the group consisting of a monoalkylene glycol monoester of methacrylic acid, a polyalkylene glycol monester of methacrylic acid, a monoalkylene glycol monoester of crylic acid, a polyalkylene glycol monoester, a N-alkyl substituted acrylamide, a N,N-dialkyl substituted acrylamide, a N-alkyl substituted methacrylamide, a N,N-dialkyl substituted methacrylamide, N-vinylpyrrolidone, an alkyl substituted N-vinylpyrrolidone, and vicinal epoxy alkyl 2-alkenoate, characterized by: water-insolubility; water-swellability; biological inertness; non-toxicity to and compatibility with living tissue; retention of structural integrity over long periods of time in contact with body fluids; a water-uptake capability when in osmotic equilibrium with water of from 5 to 4000 weight percent based on the weight of said hydrophilic material to form a hydrogel; an ultimate strength of about 3 $g/mm^2$ to 200 $g/mm^2$, an initial tear strength of 0.1 $g/mm^2$ to 20 $g/mm^2$, and a progagation tear strength of 0.5 g/mm to 10 g/mm; and 3-dimensional, reticulum-like porosity in which at least about 75 percent of the remaining pores, as determined under a scanning electron microscope, are characterized by an average diameter, not exceeding about 10 microns and in which below about 25 percent of the pores are characterized by an average diameter generally sufficiently small so as to prevent an immune rejection when said hydrophilic material containing biologically active tissue therein is in contact with living tissue environment, the geometry of such permitting the ingress or egress of a steroid.

2. The hydrophilic material as claimed in claim 1 wherein below about 25 percent of the average diameter of said remaining pores does not exceed about 20$\mu$.

3. The hydrophilic material as claimed in claim 2 in which its thickness is in the range of from about 100$\mu$ to about 1000$\mu$.

4. The hydrophilic material as claimed in claim 1 characterized by a water uptake capability of about 20 to about 2000 weight percent.

5. The hydrophilic material as claimed in claim 1 in which its thickness is in the range of from about 30$\mu$ to about 1000$\mu$.

6. The hydrophilic material as claimed in claim 5 in equilibrium with living tissue environment and characterized by the non-ingress of viable cellular entities therein and the egress of viable hormones therefrom.

7. The hydrophilic material as claimed in claim 5 which is a polymer comprised of recurring units of an alkylene glycol monoester of methacrylic acid in its polymeric chain.

8. The hydropholic material as claimed in claim 7 wherein said alkylene glycol monoester of methacrylic acid is 2-hydroxyethyl methacrylate.

9. The hydrophilic material as claimed in claim 1 wherein said polymer is comprised of at least the monomer which is a monoakylene glycol monoester of methacrylic acid.

10. The hydrophilic material as claimed in claim 1 wherein said polymer is comprised of at least the monomer which is a polyalkylene glycol monoester of methacrylic acid.

11. The hydrophilic material as claimed in claim 1 wherein said polymer is comprised of at least the monomer which is a monoakylene glycol monoester of acrylic acid.

12. The hydrophilic material as claimed in claim 1 wherein said polymer is comprised of at least the monomer which is a polyalkylene glycol monoester of acrylic acid.

13. The hydrophilic material as claimed in claim 1 wherein said polymer is comprised of at least the monomer which is a N,N-dialkyl substituted methacrylamide.

14. The hydrophilic material as claimed in claim 1 wherein said polymer is comprised of at least the monomer which is a N-alkyl substituted methacrylamide.

15. The hydrophilic material as claimed in claim 1 wherein said polymer is comprised of at least the monomer which is a N,N-dialkyl substituted acrylamide.

16. The hydrophilic material as claimed in claim 1 wherein said polymer is comprised of at least the monomer which is a N-alkyl substituted acrylamide.

17. The hydrophilic material as claimed in claim 1 wherein said polymer is comprised of at least the monomer which is N-vinylpyrrolidone.

18. The hydrophilic material as claimed in claim 1 wherein said polymer is comprised of at least the monomer which is an alkyl substituted N-vinylpyrrolidone.

19. The hydrophilic material as claimed in claim 1 wherein said polymer is comprised of at least the monomer which is a vicinal epoxy alkyl 2-alkenoate.

20. The material as claimed in claim 1 in the form of a chamber.

21. The chamber as claimed in claim 20 in the form of a pouch, sheet, laminate, capsule or membrane.

22. The chamber as claimed in claim 20 in the form of a pouch.

23. The chamber as claimed in claim 20 in the form of a sheet.

24. The chamber as claimed in claim 20 in the form of a laminate.

25. The chamber as claimed in claim 20 in the form of a capsule.

26. The chamber as claimed in claim 20 in the form of a membrane.

27. The device comprised of the chamber as claimed in claim 20 and particulate biologically active tissue contained therein.

28. The device as claimed in claim 27 wherein said biologically active tissue is viable pancreatic tissue.

29. The device as claimed in claim 27 in contact with body tissue and in osmotic equilibrium with body fluid thus permitting body nutrients from the body fluid to ingress into the device with the concomitant egress of biological active secretants produced from the biologically active tissue and nutrients to egress therefrom.

30. The device as claimed in claim 29 wherein said biologically active tissue is pancreatic tissue.

31. The material as claimed in claim 5 in the form of a chamber.

32. The chamber as claimed in claim 31 in the form of a pouch, membrane, laminate, sheet or capsule.

33. The device comprised of the chamber as claimed in claim 21 and particulate biologically active tissue contained therein.

34. The device as claimed in claim 33 in contact with body tissue and in osmotic equilibrium with body fluid thus permitting body nutrients from the body fluid to ingress into the device with the concomitant egress of biological active secretants produced from the biologically active tissue and nutrients to egress therefrom.

35. The device as claimed in claim 34 wherein said biologically active tissue is pancreatic tissue.

36. The material as claimed in claim 7 in the form of a chamber.

37. The device comprised of the chamber as claimed in claim 36 and particulate biologically active tissue contained therein.

38. The material as claimed in claim 8 in the form of a chamber.

39. The chamber as claimed in claim 30 in the form of a pouch, membrane, laminate, or capsule.

40. The device comprised of a membranous chamber as claimed in claim 31 and particulate biologically active tissue contained therein.

41. The device as claimed in claim 40 wherein said biologically active tissue is viable pancreatic tissue.

42. The device as claimed in claim 40 in contact with body tissue and in osmotic equilibrium with body fluid thus permitting body nutrients from the body fluid to ingress into the device with the concomitant egress of biological active secretants produced from the biologically active tissue and nutrients to egress therefrom.

43. The device as claimed in claim 42 wherein said biologically active tissue is pancreatic tissue.

* * * * *